(12) United States Patent
Pemba et al.

(10) Patent No.: US 10,064,565 B2
(45) Date of Patent: Sep. 4, 2018

(54) MULTIELECTRODE ARRAY AND METHOD OF FABRICATION

(71) Applicant: The Regents of the University of California, Oakland, CA (US)

(72) Inventors: Dhonam Pemba, Toluca Lake, CA (US); William C. Tang, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/533,882

(22) Filed: Nov. 5, 2014

(65) Prior Publication Data

US 2015/0126843 A1 May 7, 2015

Related U.S. Application Data

(60) Provisional application No. 61/900,260, filed on Nov. 5, 2013.

(51) Int. Cl.
*A61B 5/04* (2006.01)
*A61B 5/00* (2006.01)
*A61N 1/05* (2006.01)
*G03F 7/038* (2006.01)

(52) U.S. Cl.
CPC .......... *A61B 5/04001* (2013.01); *A61B 5/686* (2013.01); *A61N 1/05* (2013.01); *G03F 7/038* (2013.01); *A61B 2562/028* (2013.01); *A61B 2562/12* (2013.01)

(58) Field of Classification Search
CPC ........ A61B 5/04001; A61B 5/686; A61N 1/05
USPC .................................................. 600/377, 378
See application file for complete search history.

(56) References Cited

U.S. PATENT DOCUMENTS

| | | | |
|---|---|---|---|
| 7,326,649 B2 | 2/2008 | Rodger et al. | |
| 8,283,569 B2 | 10/2012 | Johnson et al. | |
| 8,355,768 B2* | 1/2013 | Masmanidis | A61B 5/04001 600/372 |
| 8,498,720 B2 | 7/2013 | Pellinen et al. | |
| 8,805,467 B2* | 8/2014 | Yobas | A61B 5/04001 600/377 |
| 8,927,876 B2 | 1/2015 | Johnson et al. | |

(Continued)

FOREIGN PATENT DOCUMENTS

EP    2452707 A1    5/2012

OTHER PUBLICATIONS

Takecuchi et al "Parlene flexible . . . channels", Lab Chip, 2005,5, 519-523.*

(Continued)

*Primary Examiner* — Lee S Cohen
(74) *Attorney, Agent, or Firm* — Archer Norris, PLC; Sean D. Senn; Priti D. Phukan

(57) ABSTRACT

A multielectrode array with a fluidic channel and its method of fabrication are presented here. In accordance with various embodiments, the present invention allows for scalability, reproducibility, and precision dimension control by utilizing a lithography dependent process. In one embodiment, the present invention provides for a microelectrode that is a neural implant, with the microelectrode configured for connection to a fluidic channel. In another embodiment, the fluidic channel may deliver growth factors and/or drugs.

8 Claims, 24 Drawing Sheets

(56) References Cited

U.S. PATENT DOCUMENTS

| | | | | |
|---|---|---|---|---|
| 9,014,796 B2* | 4/2015 | Kipke | ............... | A61B 5/04001 600/544 |
| 2006/0212097 A1* | 9/2006 | Varadan | ................ | A61B 5/031 607/62 |
| 2013/0211485 A1* | 8/2013 | Govindarajan | .......... | A61N 1/05 607/116 |
| 2014/0107446 A1* | 4/2014 | Tolosa | ............... | A61B 5/04001 600/345 |
| 2014/0378993 A1* | 12/2014 | Shah | ................... | A61N 1/0551 606/129 |

OTHER PUBLICATIONS

Abgrall et al., A Novel Fabrication Method of Flexible and Monolithic 3D Microfluidic Structures Using Lamination SU-8 Films, Journal of Micromechanic and Microengineering (2006), pp. 113-121, 16.

Altuna et al., SU-8 Based Microneedles for In Vitro Neural Applications, Journal of Micromechanics and Microengineering (2010), pp. 064014, 20.

Bartels et al., Neurotrophic Electrode: Method of Assembly and Implantation Into Human Motor Speech Cortex, Journal of Neuroscience Methods (Sep. 30, 2008), pp. 168-176, 174(2).

Fallon et al., In Vivo Induction of Massive Proliferation, Directed Migration, and Differentiation of Neural Cells in the Adult Mammalian Brian, Proceedings of the National Academy of Sciences (Dec. 19, 2000), pp. 14686-14691, 97 (26).

Frey et al., Biosensor Microprobes With Integrated Microfluidic Channels for Bi-Directional Neurochemical Interaction, Journal of Neural Engineering (2011), 8(6).

Huang et al., Parylene Coated Silicon Probes for Neural Prosthesis, Proceedings of the 3rd IEEE International conference on Nano/Micro Engineered and Molecular Systems (Jan. 6-9, 2008), pp. 947-950.

Kuo et al., Novel Flexible Parylene Neural Probe With 3D Sheath Structure for Enhancing Tissue Integration, Lab on a Chip (2013), pp. 554-561, 13.

Seidl et al., In-Plane Silicon Probes for Simultaneous Neural Recording and Drug Delivery, Journal of Micromechanics and Microengineering (2010), 20.

Spieth et al., Robust Microprobe Systems for Simultaneous Neural Recording and Drug Delivery, 4th European Conference of the International Federation for Medical and Biological Engineering (ECIFMBE) (2008), pp. 2426-2430, 22.

Terenghi, Giorgio, Peripheral Nerve Regeneration and Neurotrophic Factors, Journal of Anatomy (2002), pp. 1-14, 194 (1).

* cited by examiner

MULTIELECTRODE ARRAY AND METHOD OF FABRICATION

CROSS-REFERENCE TO RELATED APPLICATIONS

The present application claims the benefit of priority under 35 U.S.C. §119(e) of provisional application Ser. No. 61/900,260 filed Nov. 5, 2013, the contents of which are hereby incorporated by reference.

FIELD OF USE

The present invention relates to the technical field of multielectrodes. More particularly, the present invention is in the technical field of neural implants. More particularly, the present invention is in the technical field of implantable microelectrodes for reading physiological signals within a body.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Neural implants have emerged over the last few decades as a possible means to interact directly with our nervous system. By bridging the gap between our nervous system and the external environment, a neural implant system can potentially replace neural functions and treat neural disorders. Electrodes are one of the key components of neural implant systems that allow the electrical stimulation and recoding of activity of our neurons. The advancement of Micro-Electro Mechanical Systems (MEMS) has made the realization of microelectrodes possible. The key advantages of using MEMS fabricated electrodes over traditional metal wire electrodes are batch fabrication, improved reproducible geometry and electrical characteristics, smaller feature size, and the capabilities for on-chip circuitry.

Although microelectrodes have demonstrated success, their short lifespans are a barrier to clinical practicality. Microelectrodes typically last less than a year due to cellular responses upon implantation. Within the last decade there have been efforts to include fluidic channels in electrodes. The incorporation of fluidic channels would not only allow for simulation electrophysiological measurements but also the capability to delivery drugs that enhance nerve regeneration and prevent reactive cellular response.

Microelectrodes with fluidic delivery capabilities could not only prevent these reactive cellular responses but also allow for electrophysiological measurements and the capability to delivery drugs that enhance nerve regeneration. Fluidic channels were fabricated in the traditional Michigan probes by using shallow boron diffusion to define the channel mask, reactive ion etching to etch the channel, ethylene diamine and pyrocatecho to form a continues flow channel by undercutting the mask, and growing and depositing dielectrics to seal the channel. Other groups have similarly used sacrificial layers and sealants to construct fluidic neural probes. An alternative to sealing the channel with dielectrics or using sacrificial materials is bonding the channel roof to walls of microchannel. The limitation of bonding technique occurs from low adhesion strength, poor alignment. Fluidic channels fabricated with sacrificial layers and dielectric sealing methods are limited by deliverable volume. The challenge in multielectrode fabrication efforts today is developing processes that allows for scalability, reproducibility, and precision dimension control.

SUMMARY OF THE INVENTION

The present invention is a multielectrode with/without fluidic delivery capability. The description provided are without limitation to the embodiments described, but represent preferred embodiments.

In the preferred embodiment an implantable microelectrode is described with a fluid channel whose configuration were developed to mitigate the immune response, tissue encapsulation, and/or enhance neural growth or peripheral nerves. Novel methods of making and using the same are also described.

In the presented embodiments, without limitation, the invention consists of a microelectrode having at least one electrode site and embedded fluidic channel.

In first preferred embodiment, the invention comprises of the microelectrode having a shank and fluidic channel both constructed out of the negative photoresist, SU-8. In such an embodiment, at least one electrode site is on the surface of a SU-8, and a fluidic channel comprised out of SU-8 is embedded within the multielectrode.

In second preferred embodiment, the invention comprises of a microelectrode with at silicon shank and at least one electrodes site, wherein the shank comprises as the backbone of the implant. In this described embodiment, on the opposite side of the electrode surface consist of a fluidic channel constructed out of SU-8, the channel wall and roof could entirely consist of the negative photoresist, SU-8, in such an embodiment, at least one electrode site is on the surface of a silicon shank, and a fluidic channel comprised out of SU-8 is on the opposite surface.

Novel methods of partially sealing fluidic channel, manufacturing electrode sites, and device separation of microelectrodes will be presented. Dimensions of the probes are defined by current material and equipment limitations, where further scaling will become apparent from the details provided herein.

DETAILED DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Hornyak, et al., Introduction to Nanoscience and Nanotechnology, CRC Press (2008); Singleton et al., Dictionary of Microbiology and Molecular Biology 3rd ed., J. Wiley & Sons (New York, N.Y. 2001); March, Advanced Organic Chemistry Reactions, Mechanisms and Structure 7th ed., J. Wiley & Sons (New York, N.Y. 2013); and Sambrook and Russel, Molecular Cloning: A Laboratory Manual 4th ed., Cold Spring Harbor Laboratory Press (Cold Spring Harbor, N.Y. 2012), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

One skilled in the art will recognize many methods and materials similar or equivalent to those described herein, which could be used in the practice of the present invention. Indeed, the present invention is in no way limited to the methods and materials described.

Figure 1:
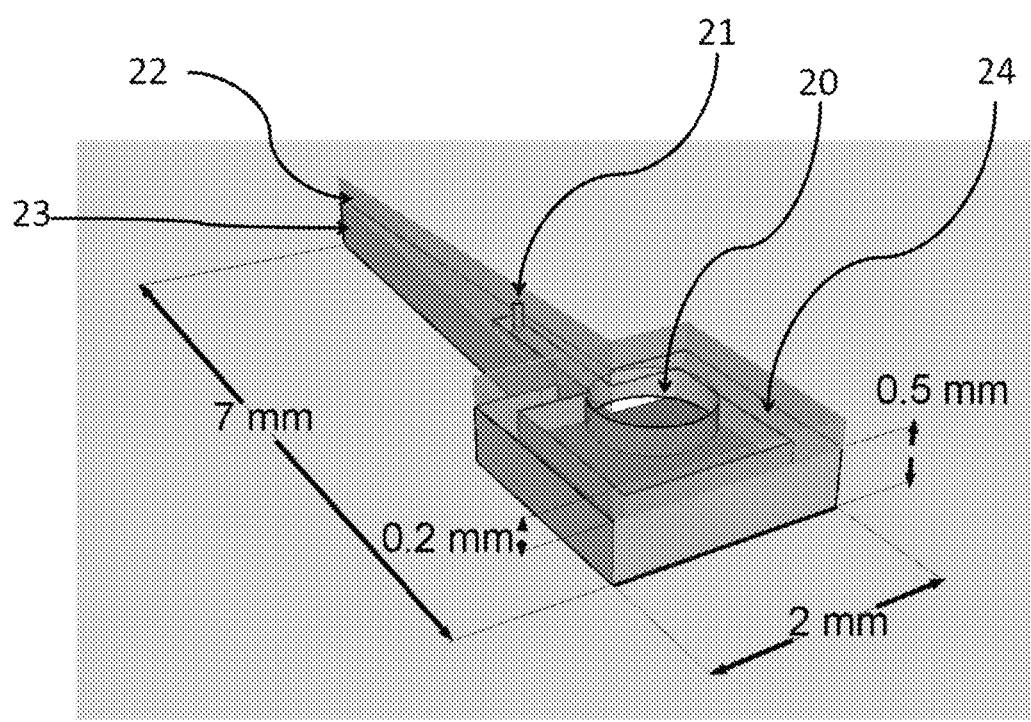
FIG. 1, in accordance with an embodiment herein, is a three dimensional view of the microelectrode in accordance with second preferred embodiment of the invention FIG. 2, in accordance with an embodiment herein, is a three dimensional view of the microelectrode in accordance with first preferred embodiment of the invention.

In one embodiment, the present invention is described in FIG. 1 and there is multielectrode array. 23 shows the silicon shank attached to a SU-8 structure with an embedded fluidic channel. 21 and 20 represent the outlet and inlet of the embedded fluidic channel, respectively. The 22 represents SU-8 layer that defines the SU-8 shape and channel walls, and 24 represents the SU-8 layer that forms the roof of the channels, inlet and outlet.

Figure 2:
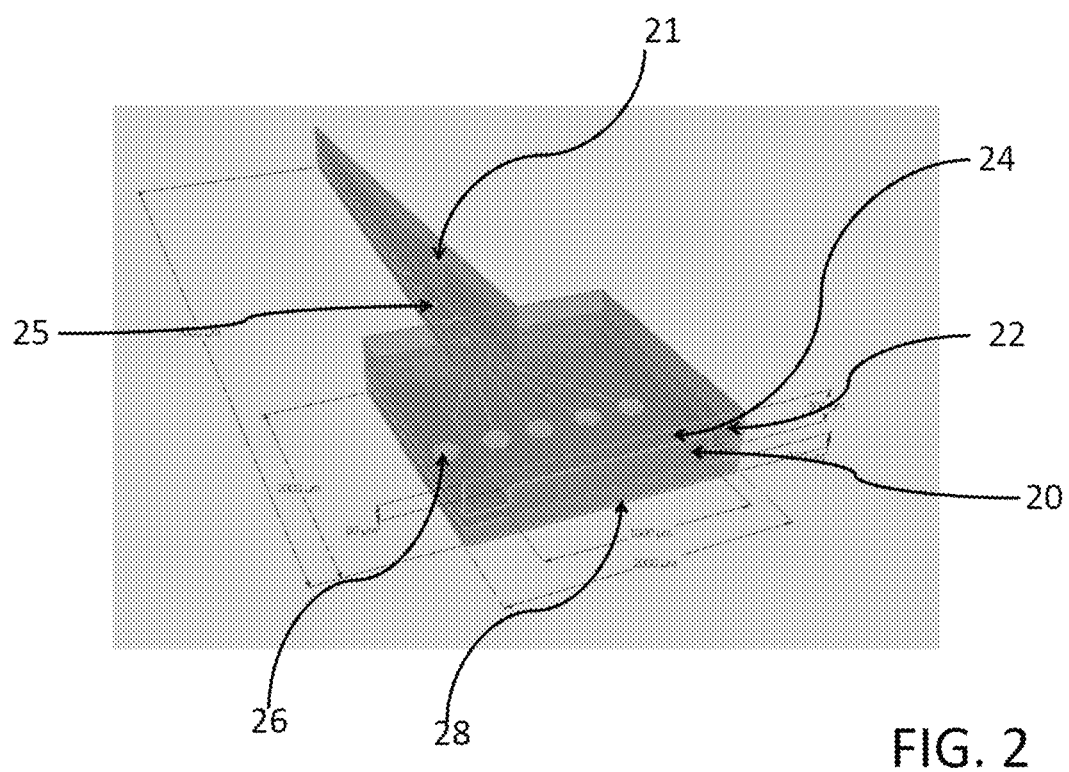

Referring now to the embodiment shown in FIG. 1 and FIG. 2 there is multielectrode array. 28 show the bottom layer of SU-8 which serves as the floor of the fluidic channel and the probe shape. Electrode bond pads, 26 and electrode sites, 25 are attached on the surface away from center of 28, 21 and 20 represent the outlet and inlet of the embedded fluidic channel, respectively. The 22 represents SU-8 layer that defines the SU-8 shape and channel walls and 24 represents the SU-8 layer that forms the roof of the channels, inlet and outlet.

In another embodiment, as described in FIG. 1 and FIG. 2, the electrode sites 25 interface with entities in the central and peripheral nervous system to either record electrical activity, or stimulate entities. These entities could include neurons, nerves, cells, and other biological components that react to or produce electrical activity. The electrode bond pads 26 interface with external electrical components that could include wires and circuitry. The fluidic channel connected between 21 and 20 represents the channel for fluid and drug delivery. The inlet 20 could be positioned in different orientations as it is orthogonal in FIG. 1 and parallel in FIG. 2 to the fluidic channel. In the same manner, the outlet 21 could be orthogonal or parallel to the fluidic channel. Fluid can be injected from the inlet 20 to the outlet 21 to for applications that include electrophysiological experiments, drug delivery to enhance nerve regeneration, and chemical release to prevent reactive cellular response.

Figure 3:
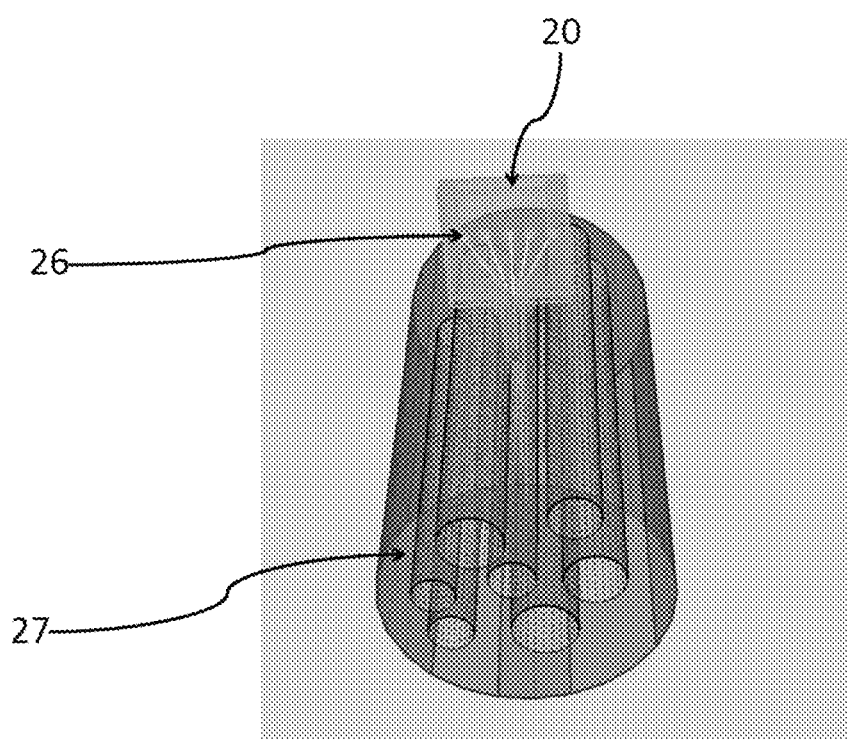
FIG. 3, in accordance with an embodiment herein, is a three dimensional view of the microelectrode implanted in peripheral nerve in accordance with one embodiment of the invention FIG. 4, in accordance with an embodiment herein, is a top view of photolithography mask design in accordance with one embodiment of the invention.

FIG. 3 provides an example of how the embodiment described in FIG. 1 and FIG. 2 might interface with a nerve of the peripheral nervous system.

Figure 4:
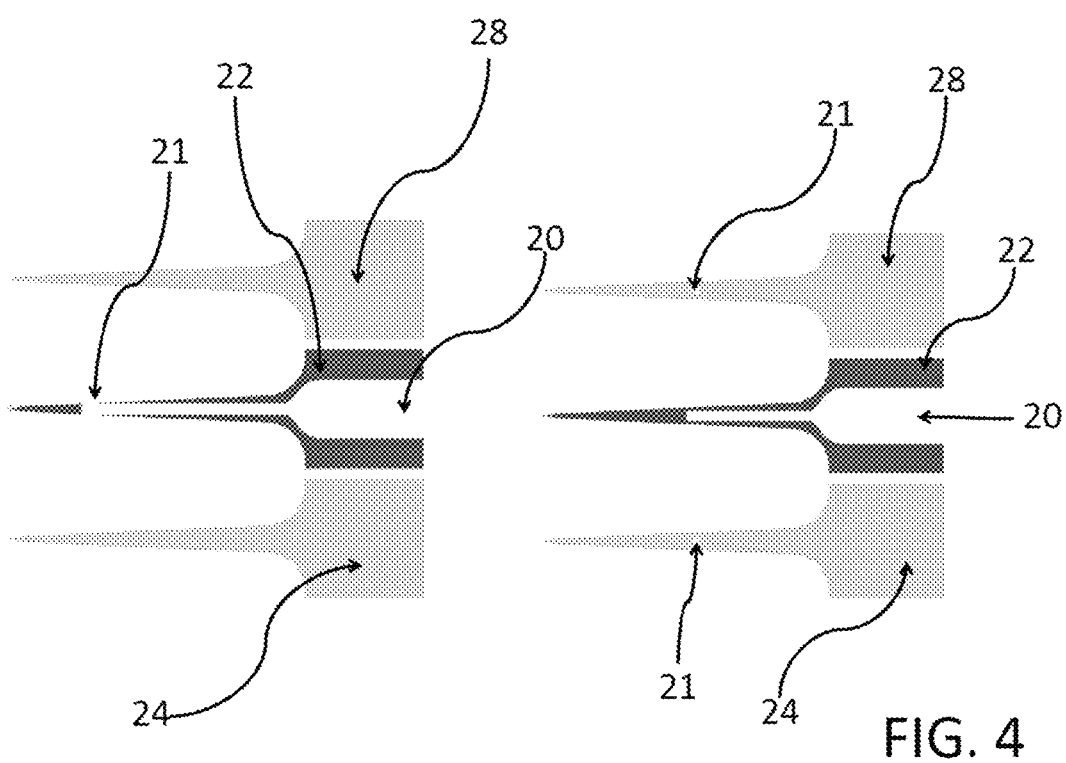

Layouts in FIG. 4 provide details on construction of the device shown in FIG. 2. The layouts are provided as an example to illustrate the construction of the device, but not to limit the design. A person skilled in the art would readily be able to design different layouts for other specifications. The layout designs are reversed in polarity, as the physical mask would have the white area are of the layout to be opaque to ultraviolet light, while the filled in regions of the layout would be clear and transparent to ultraviolet light in the physical mask. SU-8 is a negative resist, which means that that regions exposed to ultraviolet light would remain. 28 would form the floor of the fluidic channel and electrode shape. 22 would produce the channel walls and also the electrode shape. 24 would produce the channel roof, inlet and outlet. The image on the right of FIG. 4 illustrates that in 21, ultraviolet light would not reach the circular region as that region would be opaque in the physical mask, and therefore create the orthogonal outlet. Likewise, orthogonal inlets could be constructed in the same manner. In FIG. 4, the outlet 20 continues beyond the edge of the electrode shape, and thus creates an parallel inlet to the channel. The image in the middle left of FIG. 4 demonstrates parallel outlet as 21 extends beyond the electrode shape.

Figure 5:
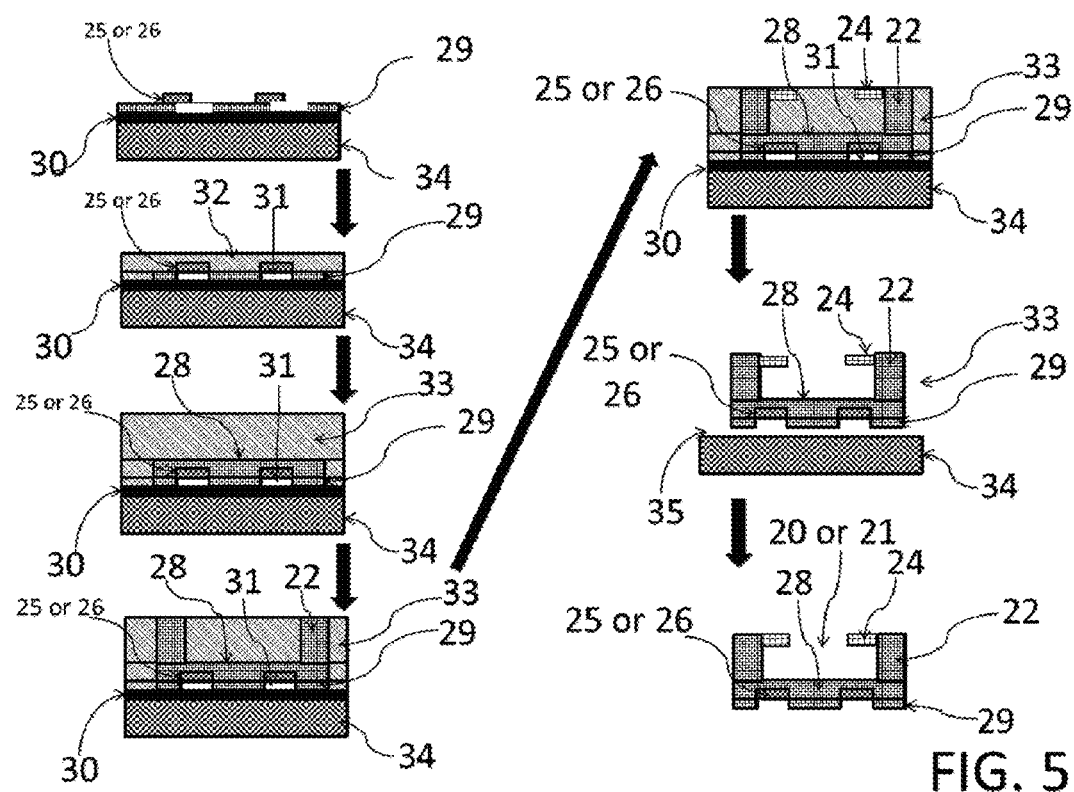
FIG. 5, in accordance with an embodiment herein, is a cross-sectional views manufacturing process of first preferred embodiment of the invention.

The construction details of an embodiment described in FIG. 2 is shown in FIG. 5

The first step is to deposit a sacrificial layer 30 (example would be 2 μm of oxide) on a carrier substrate, 34 (example would be silicon wafer). The next step would be to pattern a dielectric layer, 29, that will not be resistant to the etching of the sacrificial layer 30. Examples would be using oxide as the sacrificial layer and patterning SU-8 as the dielectric, or using oxide as the dielectric and aluminum as the sacrificial layer, or stoichiometric silicon nitride (SiCl2H2) as the dielectric and oxide as the sacrificial layer. Methods of patterning dielectrics and depositing the sacrificial layer are well known and established in the field of MEMS. The pattern of the dielectric layer would expose the electrode sites 25 and electrode pads 26 but protect the interconnects that connect the electrodes sites 25, to electrodes pads 26. The next step was to create the electrode sites 25, electrode pads 26 and interconnects on the dielectric 29. The inventors patterned 200 nm chrome but many other materials could be used including iridium oxide, gold, platinum, PEDOT, and carbon nanotubes, etc can be patterned by those skilled n the arts via methods that include lift-off and etching. The next step is to pattern the bottom of the channel and probe shape 28, by spinning a layer of SU-8, 32. For illustrations, 100 μm of SU-8 2050 could be spun. The probe shape and channel floor are defined 28 by crosslinking the SU-8 through ultraviolet light exposure. For example an exposure of 300 mJ/cm2 of 365 nm through a mask would define the 100 μm of SU-8 2050. The SU-8 was not developed at this time, to keep the surface planer, next another layer of SU-8 is spun 33 that would eventually be exposed to ultraviolet light to define the channel wall and probe shape 22. An example would be to spin a 300 μm layer of SU-8 2100 on top of the cross linked 100 μm of SU-8 2050 and expos it to 500 mJ/cm$^2$ of 365 nm. To define the roof, the same layer 33, was exposed wavelengths of light below 350 nm. To further illustrate, 720 mJ/cm$^2$ of 365 nm light that was filtered through a band passed 312 nm filter was used to crosslink only the top 24 of the SU-8 layer 33, and create the fluidic channel, roof 24, and inlet 20 and outlet 21. The device was developed in SU-8 developer and the crosslinked regions of SU-8 22, 24, 29 that define the multielectrode remain while the uncrosslinked regions are removed. Finally the multielectrodes are released from the carrier substrate by removing 35 the sacrificial layer 30. To illustrate again, the developed layers of SU-8 2050, and SU-8 2100 were released by soaking in buffered oxide etch. The sacrificial materials, metal layers, and dimensions can easily be changed by one of ordinary skill in the art. In addition, a SU-8 microelectrode without a fluidic channel could be easily constructed by using the above methods, creating only regions 29, 25, 26, and 28.

Figure 6:
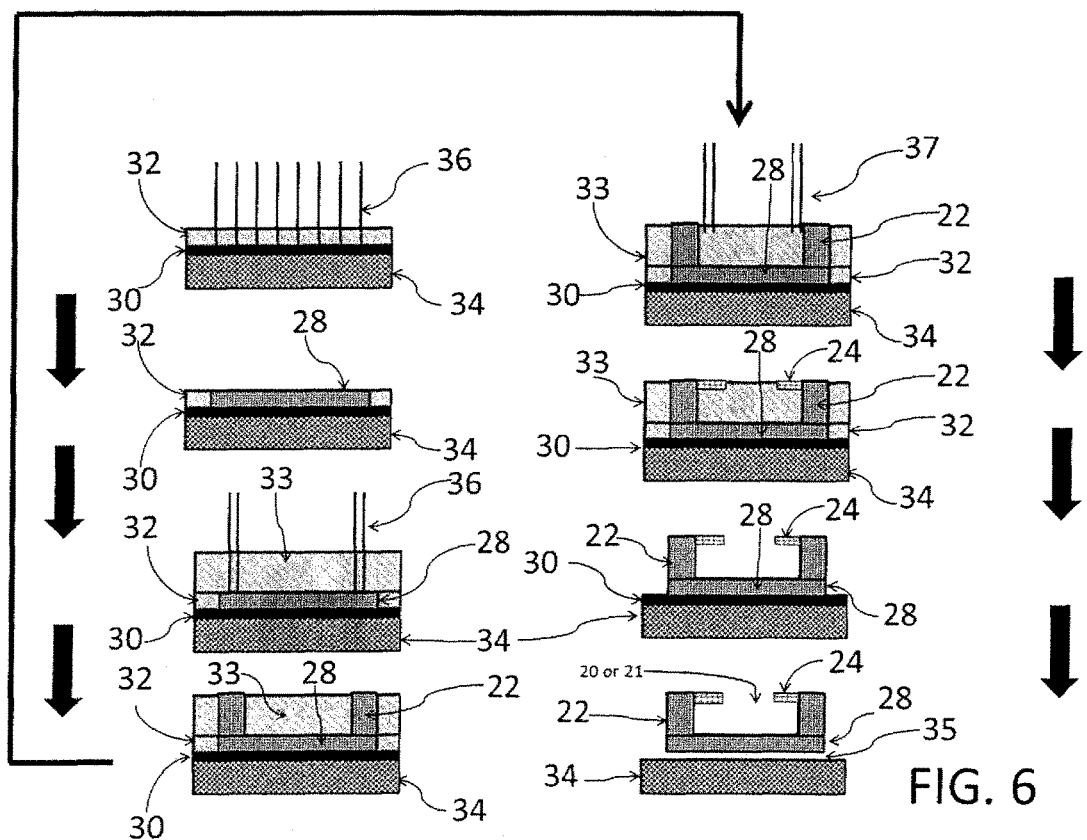
FIG. 6, in accordance with an embodiment herein, is a cross-sectional view of the embedded microchannel fabrication and release process.

FIG. 6 provides in more detail of FIG. 4, still referring to an embodiment described in FIG. 2.

There is a phenomenon known as—T-topping‖ that occurs with SU-8, where the top corners overhang. T-topping occurs due to low optical transmittance of SU-8 for wavelengths below 350 nm as wavelength below 350 nm penetrate only the surface of SU-8. This phenomenon is documented that Microchem Inc., who manufactures the SU-8 we use, suggests using a filter to eliminate wavelengths below 350 nm to obtain vertical sidewall profiles. However instead of eliminating, the lower wavelength light that is only able to penetrate the surface, it could be used to an advantage in sealing microchannels. The Higher wavelength (>350 nm) 36 penetrates all the way through the SU-8 to define the probe shape and channel walls 22 and channel floor 28, while the lower wavelength (<320 nm) 37 is used to partially crosslink upper portion of SU-8 to create the channel roof 24 and its inlets 20 and outlets 21.

Figure 7:
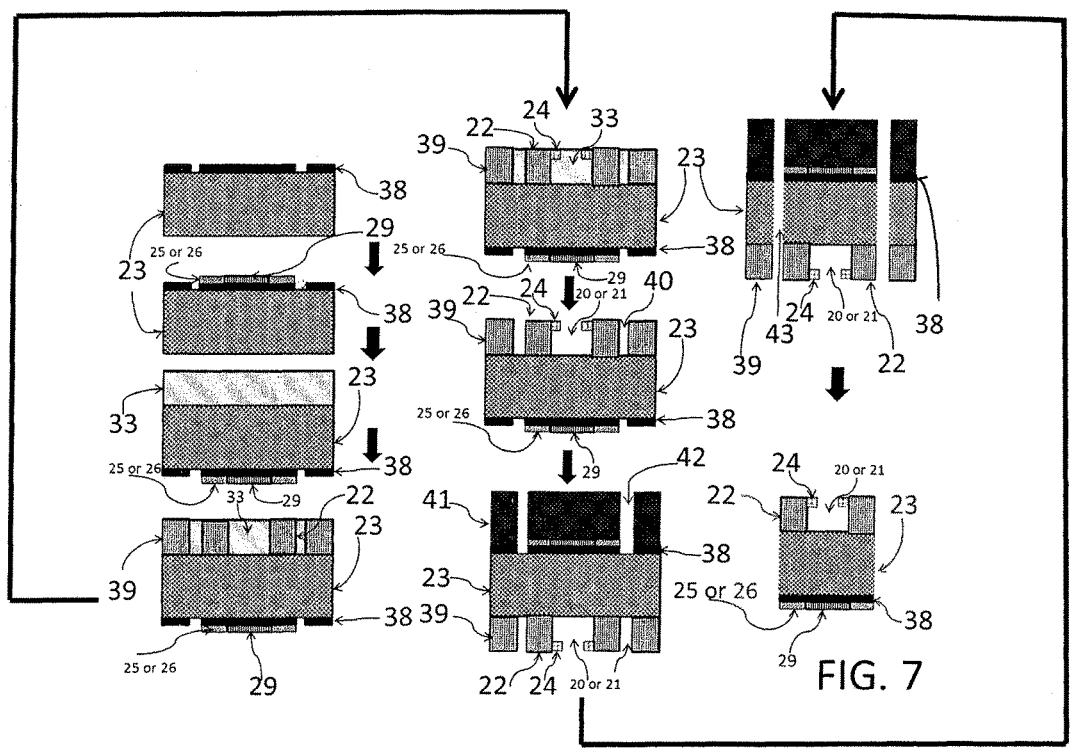
FIG. 7, in accordance with an embodiment herein, is a cross-sectional views manufacturing process of second preferred embodiment of the invention.

The construction details of the embodiment of FIG. 1 is shown in FIG. 7

Fabrication begins on a silicon wafer 23. A dielectric layer 38 first, then electrodes 25, 26 on top and then another dielectric layer 29 is patterned in the same manner as explained. A SU-8 layer 33 is spun on the opposite surface of the wafer. That layer is exposed to ultraviolet light to define the channel wall and probe shape 22. For batch fabrication, unexposed regions can exist between neighboring probe 39 and the defined probe 22. The same layer of SU-8 is then exposed to wavelength of light below 350 nm to define the roof 25, inlets and outlets. Next a mask 41 used to for deep reactive ion etching is created on the electrode side of the wafer. Deep reactive ion etching is also a well established process, but here the masking is explained for illustration. Positive photoresist is spun as the mask, and the photomask controls the regions exposed to ultraviolet light. The ultraviolet light makes the photoresist soluble to a developer, so the regions exposed to light through a photomask will removed. The removed regions cannot protect 42 the underlying silicon during etching and in doing so microelectrode features can be defined. The deep reactive ion etching is used to define the silicon multielectrode shape, which aligns with the SU-8 probe shape, to completely etch out and release the multielectrode 43.

Figure 8:
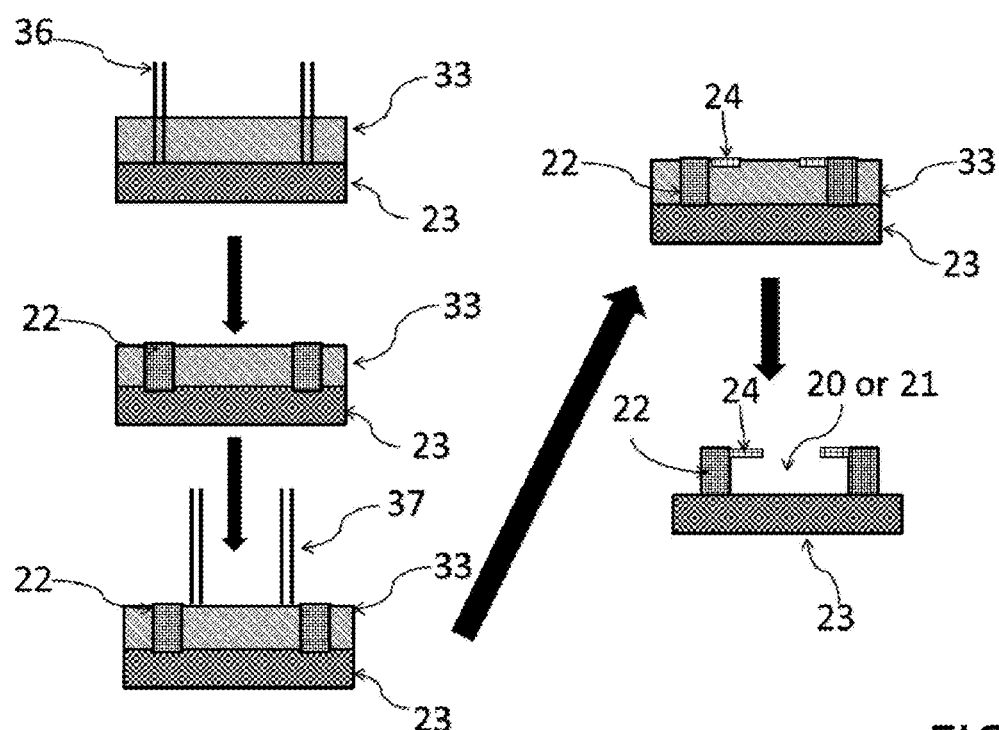
FIG. 8, in accordance with an embodiment herein, is a cross-sectional view of the embedded microchannel fabrication on the second embodiment.

FIG. 8 provides in more detail of FIG. 7, still referring to an embodiment described in FIG. 1. Similar to the explanation of FIG. 6: The Higher wavelength (>350 nm) 36 penetrates all the way through the SU-8 33 to define the probe shape and channel walls 22, while the lower wavelength (<320 nm) 37 is used to partially crosslink upper portion of SU-8 to create the channel roof 24 and its inlets 20 and outlets 21.

Figure 9:
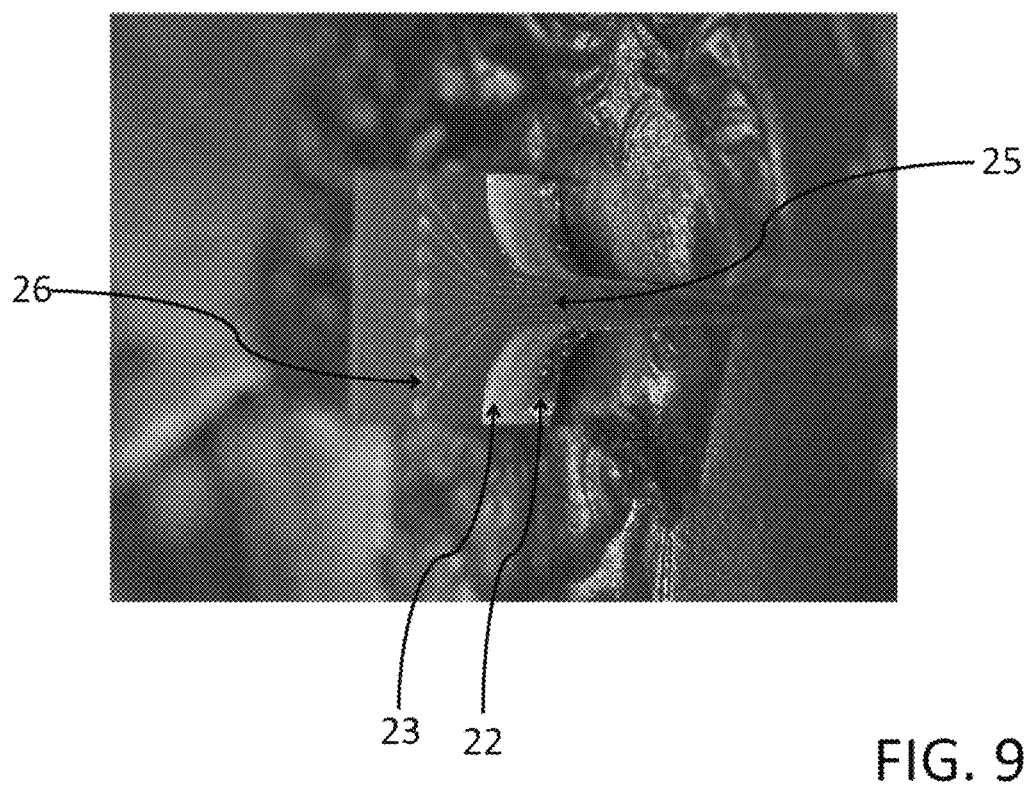
FIG. 9, in accordance with an embodiment herein, is a sample image of a fabricated silicon electrode with SU-8 fluidic channel according to second embodiment of the invention.

FIG. 9 is an example of fabricated multilectrrode of an embodiment described by FIG. 7

Figure 10:
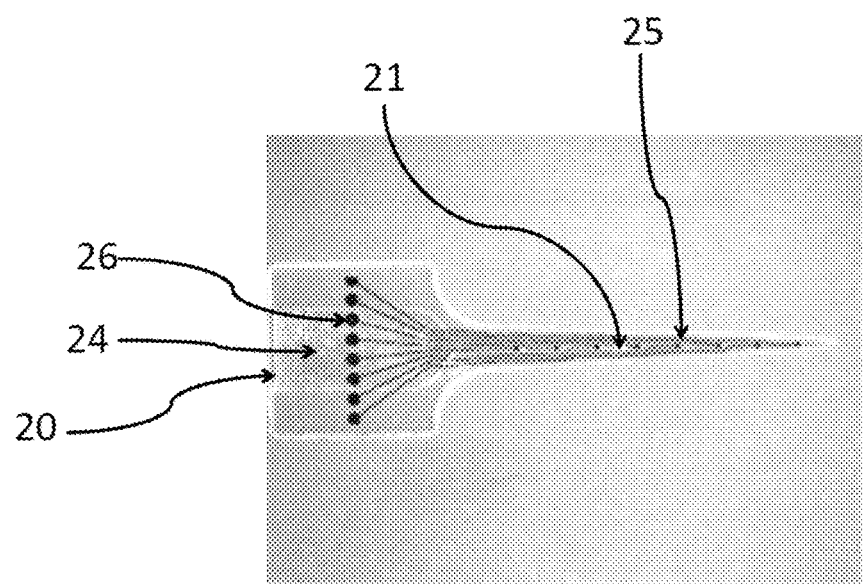
FIG. 10, in accordance with an embodiment herein, is a top view of a fabricated microelectrode according to first embodiment of the invention.
Figure 11:
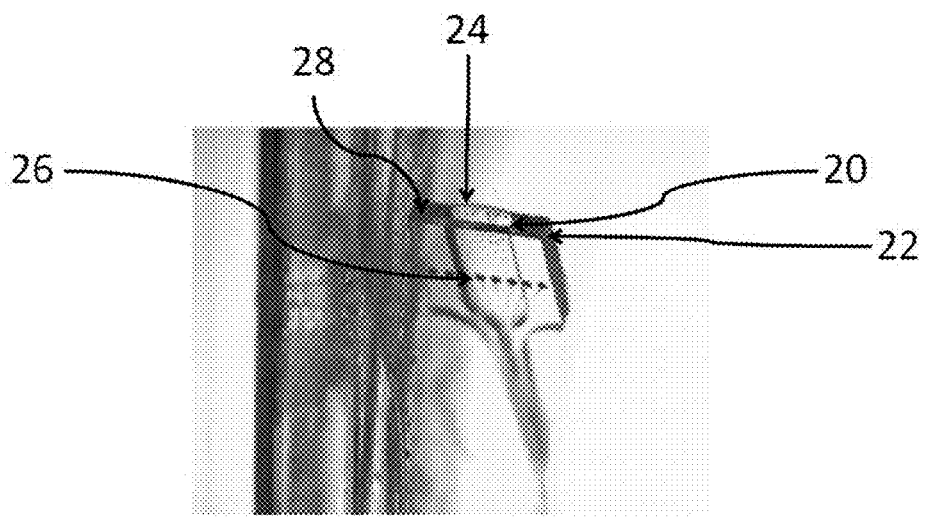
FIG. 11, in accordance with an embodiment herein, is a sample image of a fabricated microelectrode according to first embodiment of the invention.

FIG. 9 and FIG. 10 are examples of fabricated multielectrode of an embodiment described in FIG. 5. The inlet 20 is parallel to the channel which is connected to the orthogonal outlet 21. The channel roof 24, seals the microchannel.

The advantages of the present invention include, without limitation, are that it is less expensive, simpler to fabricate, can be fabricated in batches, more easily customizable, and more scalable.

In broad embodiment, the present invention is multielectrode array with/or without a fluidic channel that can be used to record/and or stimulate electrical activity to biological components.

While the foregoing written description of the embodiments enables those skilled in the art to make and use what is considered presently to be the best mode thereof, those skilled in the art will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Generally

A silicon based microelectrode with an embedded fluidic channel is developed to deliver growth factors and drugs that would mitigate the cellular responses that have limited the chronic implementation of current multielectrode arrays. Two types of silicon based microelectrodes were developed, one with the fluidic channel etched into the silicon, and SU-8 was used to make the roof. The second consist of a silicon electrode with a SU-8 fluidic channel.

A third microelectrode that is made completely out of SU-8 (Shank, and fluidic channel) was constructed. In addition to delivering drugs and growth factors, a flexible SU-8 based neural probe with fluidic and electrical capabilities was developed to further extend the longevity of neural electrodes by reducing the tissue/electrode mechanical mismatch of traditional silicon based neural electrodes. In addition to extending the life of probe, the SU-8 material is a biocompatablie insulator with the potential for MRI and other imaging compatibility.

In one embodiment, an implantable microelectrode is described with a fluid channel whose configuration were developed to mitigate the immune response, tissue encapsulation, and/or enhance neural growth or peripheral nerves. In accordance with various embodiments herein, the present invention provides for methods of making and using the same.

In another embodiment, the present invention is a microelectrode having at least one electrode site and embedded fluidic channel. In one embodiment, the invention comprises of a microelectrode with at silicon shank and at least one electrodes site, wherein the shank comprises as the backbone of the implant. In this described embodiment, on the opposite side of the electrode surface consist of a fluidic channel etched into the silicon. The channel is partially photolithographically sealed with a negative photoresist polymer resist, SU-8 to create a roof over the channel, where the etched silicon serves walls of the channel. In other embodiments, the channel wall and roof could entirely consist of the negative photoresist, SU-8, in such an embodiment, at least one electrode site is on the surface of a silicon shank, and a fluidic channel comprised out of SU-8 is on the opposite surface. In another embodiment, the invention comprises of the microelectrode having a shank and fluidic channel both constructed out of the negative photoresist, SU-8. In accordance with various embodiments herein, the present invention provides methods of partially sealing fluidic channel, manufacturing electrode sites, and device separation of microelectrodes.

Example 2

Fabrication

Three preferred embodiments of the device are presented. In the first embodiment, a silicon microelectrode consist of at least one electrode site on one surface, on the opposite surface, a silicon channel is etched using microelectromechanical system technology, and the etched channel is sealed to form the fluidic channel in the microelectrode. In the second embodiment, a silicon microelectrode consist of at least one electrode site on one surface, on the opposite side, consist of fluidic channel that was photolithogoraphically fabricated. In third embodiment, the microelectrode consist entirely out of SU-8 and consist of a Fluidic channel and at least one electrode site. In these embodiments the electrode materials can easily change by those skilled in the art. The dimensions and manufacturing specification specified in the present invention are for illustration of the preferred embodiment, and can easily be changed by those skilled in the art, and with new mask designs.

Figure 12:
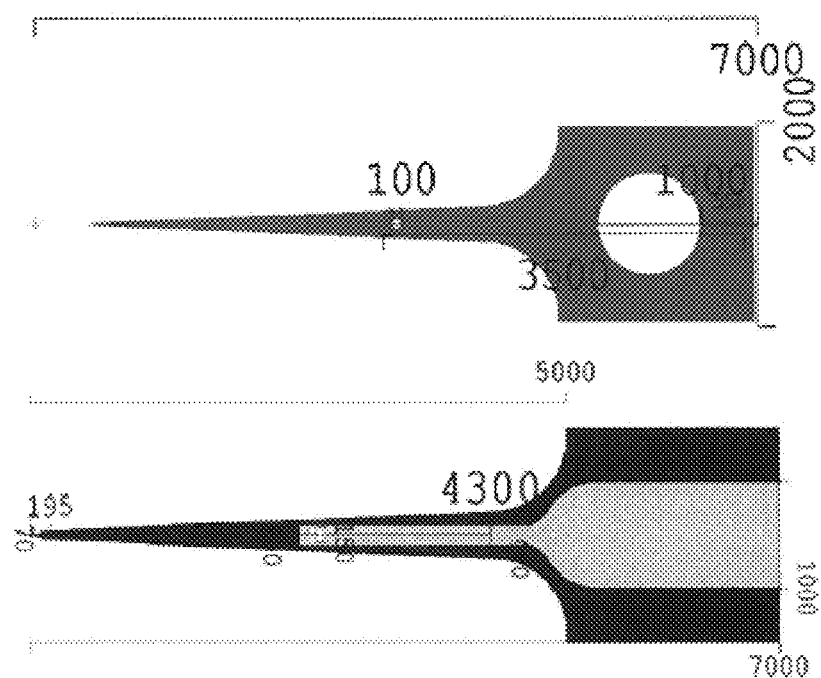
FIG. 12, in accordance with an embodiment herein, is a top view of photolithography mask design for fluidic channel in accordance with one embodiment of the invention FIG. 13, in accordance with an embodiment herein, is a cross-sectional views of topside manufacturing process of electrodes.
Figure 21:
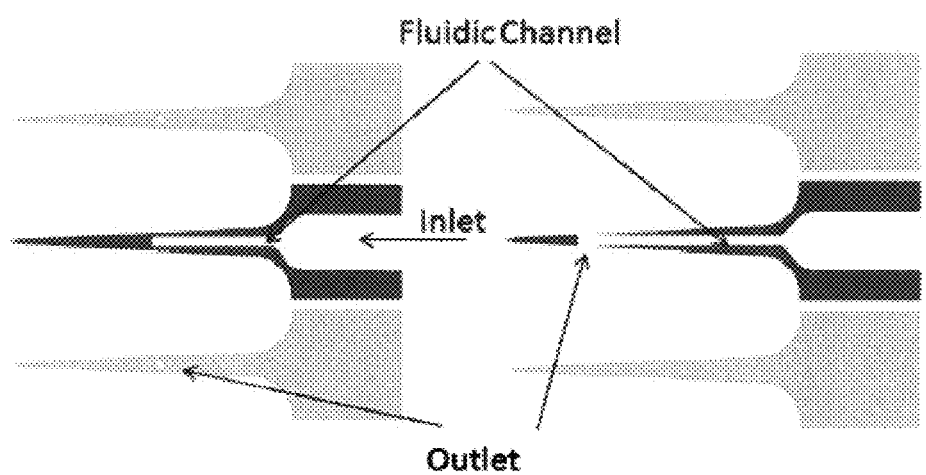
FIG. 21, in accordance with an embodiment herein, is top view of photolithography mask design in accordance with one embodiment of the invention.
Figure 22:
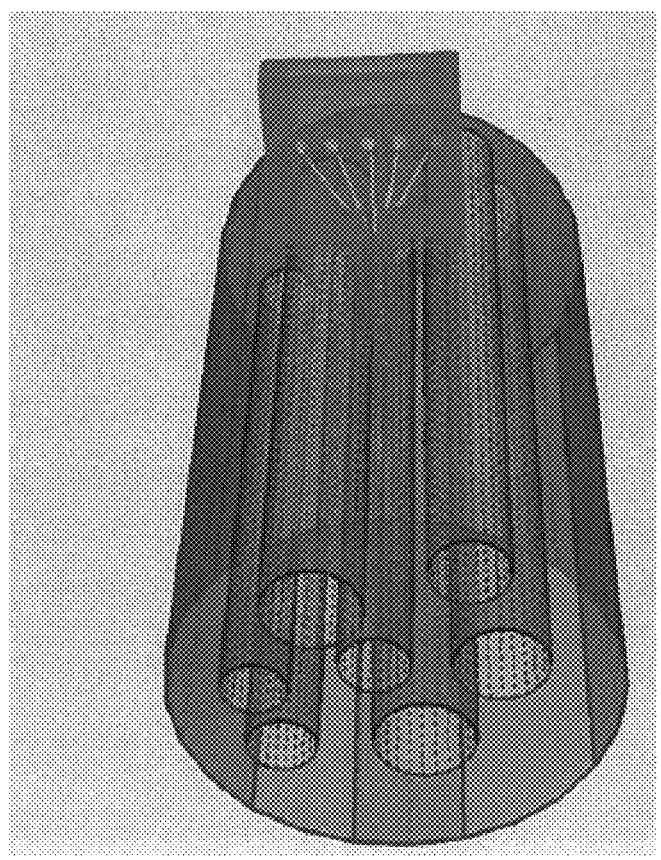
FIG. 22, in accordance with an embodiment herein, shows three dimensional view of the SU-8 microelectrode implanted in peripheral nerve in accordance with one embodiment of the invention.

FIG. 12 is the mask layout of the first two embodiments and FIG. 21 is the mask layout for the last embodiment of the invention. Positive photoresist is used as a patterned protection of the silicon during Deep Reactive Ion etching of the silicon wafer to define the probe shape. Positive photoresist is spun on a silicon wafer, and the photomask controls the regions exposed to ultraviolet light. The ultraviolet light makes the photoresist soluble to a developer, so in summary the regions exposed to light through a photomask will removed. The removed regions leave no protection during etching, and in doing so microelectrode features can be defined. The process can also be used to protect metal layers from etching to allow for definable electrode patterns. In addition, the photoresist could also be used in a process termed lift off, where the photoresist ask as sacrificial layer rather than protection. Photoresist is patterned on a wafer, and metal is deposited either via evaporation or sputtering, and the regions of the wafer that are not covered by photoresist are in contact with the deposited metal. The photoresist is then placed in solvent such as acetone, which removes the photoresist, but leaves the metal. SU-8 is negative resist that can be patterned with thickness from less than 1 micrometer to 1 mm, SU-8 features are also definable through light, but in its case, the regions exposed to light remain insoluble in development, hence its name negative resist. The printed mask of FIG. 12 is the reversed polarity as presented in the figure, hence the clear regions of the mask in FIG. 12 actually block out UV in the actual photomask. The bottom mask in FIG. 12 is used to define the channel wall, and the top mask is used to define the channel roof. These are examples of one embodiment of the invention, anyone skilled in the art can redesign the mask with their specifications. The digital image of the mask in FIG. 21 is reversed in polarity, so the shaded regions are printed clear in the physical mask. The top and bottom mask images of FIG. 21 are used to fabricate the bottom and roof of the SU-8 fluidic channel and microelectrode, while the middle image is used to fabricate the channel walls and shape.

For the first two embodiments of the invention we will refer to the Topside as the side of the silicon wafer which the electrodes are patterned, and the backside will refer to the side of the silicon wafer where the fluidic channel is constructed.

Topside Fabrication

Figure 13:
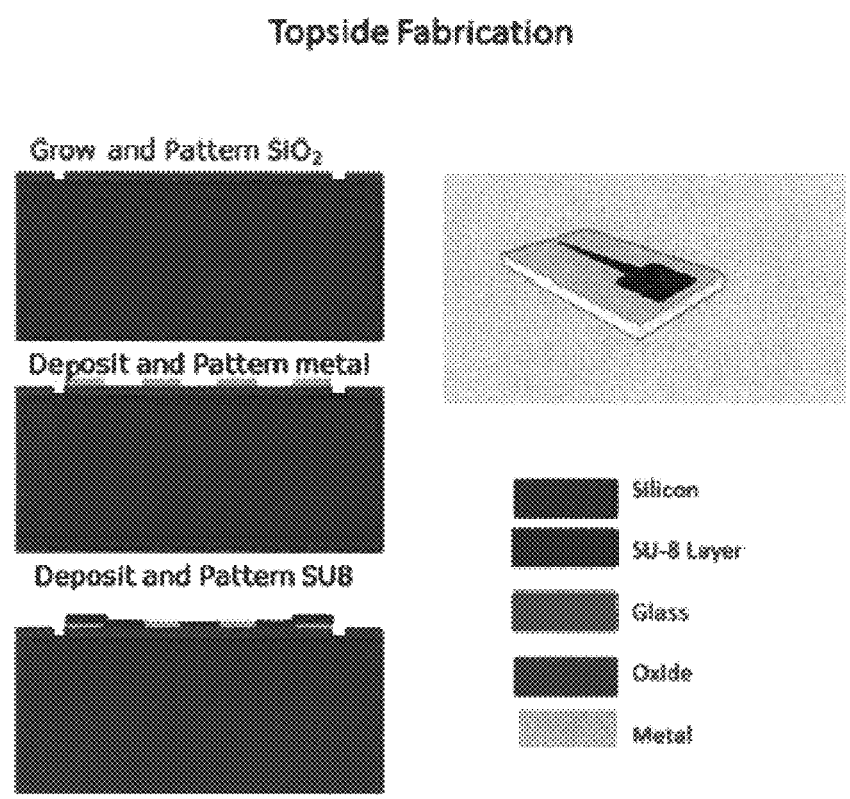

FIG. 13 details the topside fabrication process topside electrode interconnects, traces, bonding pads, and dielectrics begins by growing 0.5 μm SiO2 under thermal oxidation at 1100° to insulate the electrodes. Next gold pads, electrode sites, traces, and interconnects were patterned via lift off (Shipley 1827 3500 RPM, 30 seconds, acceleration 500 rpm/s, 10 minute bake at 95° C., 220 mJ/cm2 exposure on Karl Suss MA6 Mask Aligner, 50 seconds development using Microposit MF-319, 20 nm Ti/150 nm Au). Finally, 2 μm, SU-8 was patterned to serve as the top dielectric.

Backside Fabrication

Figure 14:
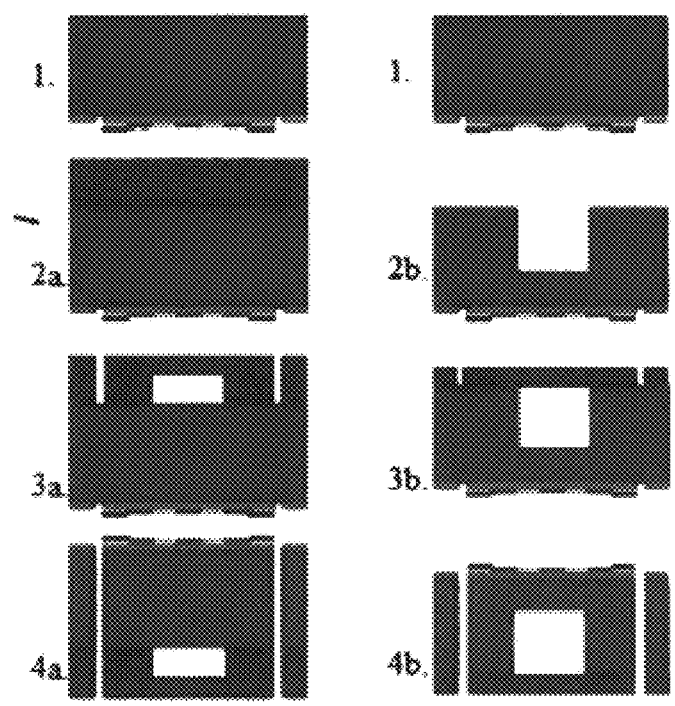
FIG. 14, in accordance with an embodiment herein, is cross-sectional views of backside and fluidic component manufacturing process of electrodes.

FIG. 14 details the fabrication process for the backside which consist of the fluidic channel and the probe shape. The fluidic channel is either etched into the wafer by the following process (FIG. 14. Right side), a positive photoresist mask was patterned to define channel shape for subsequent etching, and the initial oxide was patterned. The patterned photoresist and oxide define the mask during DRIE etching. The wafer was etched in STS DRIE until the desired depth of the channel was reached. The roof of the channel was constructed by a unique SU-8 process. In the second embodiment of the design, the fluidic channel could be defined on the surface rather than being etched inside. The process involved creating an embedded microchannel of SU-8 (FIG. 14. Left Side). The masking materials used for defining the shape in DRIE can be changed by using methods readily available to one of ordinary skill in the art.

Once the backside channel was fabricated the wafer etched and patterned from the opposite side to define the microelectrode shape and release the device. The device was mounted to a thick handle wafer using photoresist and thermal grease. Photoresist was spun on the edge of the handle wafer and thermal grease was added to the device wafer but not on the devices. The two wafers were brought in contact and placed in a 90° C. for 40 minutes. Next 15 μm AZ 4620 photoresist was patterned to define probe shape, and the initial oxide was patterned using Trion (150 mT, RIE RF 100 W, CF4 45 sccm, O2 5 sccm, He pressure 5 mT, etch time 20 minutes). The patterned photoresist and oxide define the mask during DRIE etching. The wafer was etched in STS DRIE until each probe separated (approximately 165 minutes). The probes were soaked in acetone for 30 minutes, then isopropanol for 2 days to remove photoresist, and Finally 10 minutes in ultrasonic bath to remove any final residual photoresist. The processing parameters described above were for developed for an embodiment of the invention using the available facilities and equipment, could adjust masking materials, etching devices.

SU-8 Channel Fabrication Process

Figure 15:
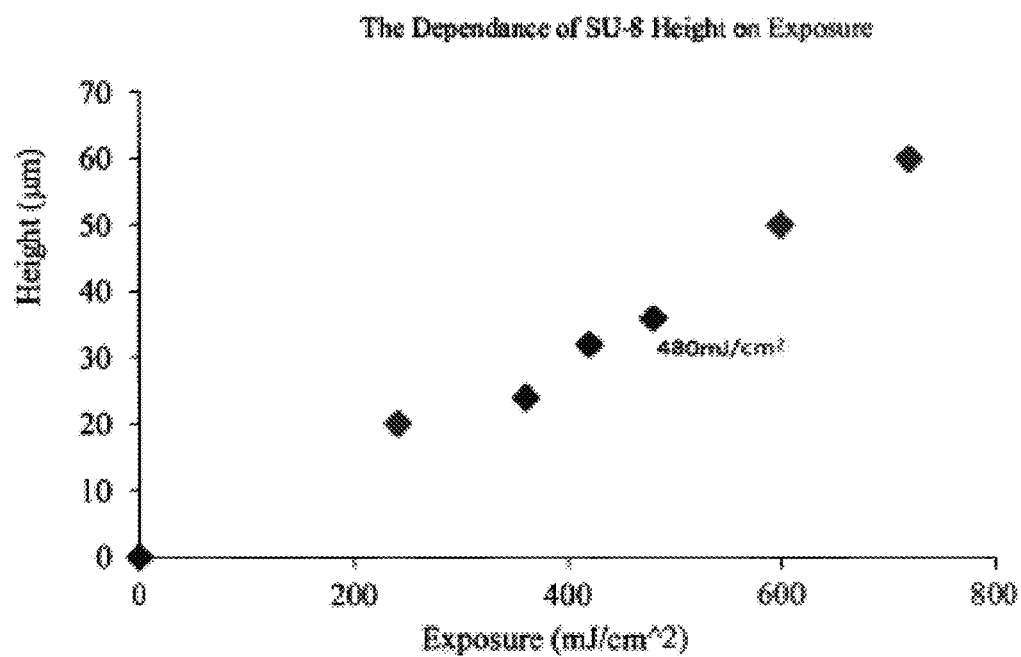
FIG. 15, in accordance with an embodiment herein, is graph that displays characterization of 312 nm filter.
Figure 16:
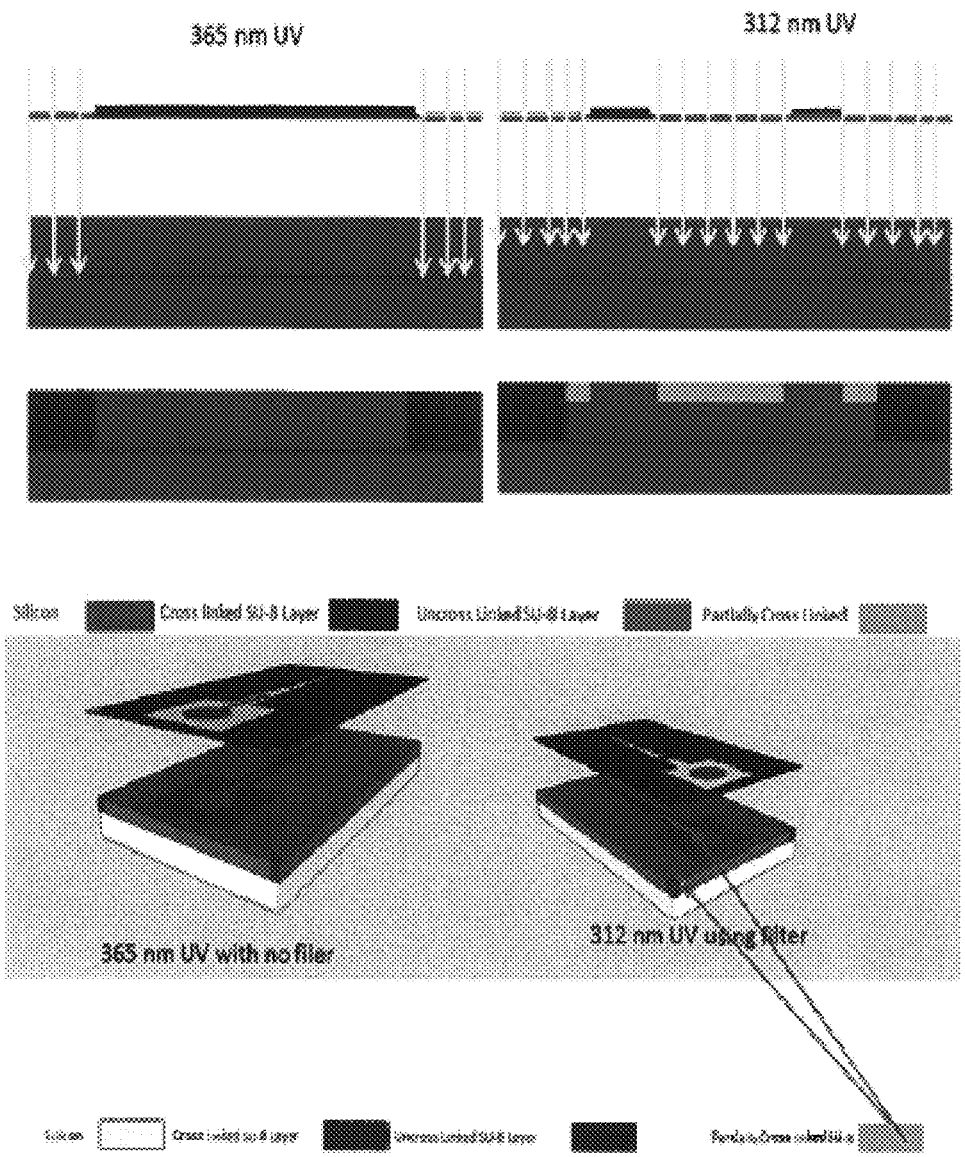
FIG. 16, in accordance with an embodiment herein, shows example of UV filtered light to partially crosslink upper portion of SU-8, and FIG. 5 provides cross section view of fluidic channel fabrication.
Figure 17:
FIG. 17, in accordance with an embodiment herein, shows sample image of a fabricated silicon electrode with SU-8 fluidic channel according to one embodiment of the invention.
Figure 18:
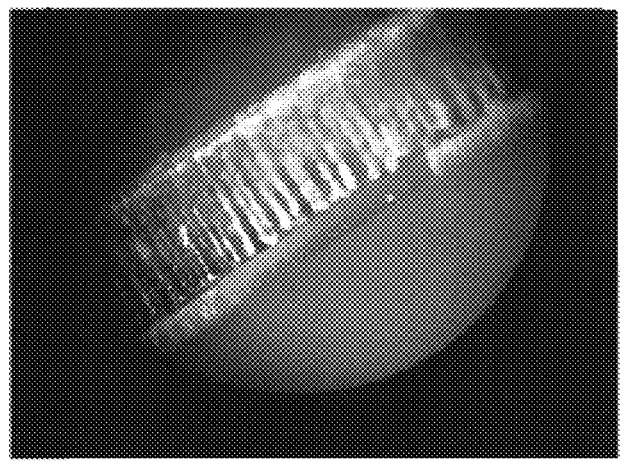
FIG. 18, in accordance with an embodiment herein, shows sample cross section image of the inlet to the fluidic channel of a fabricated silicon electrode with SU-8 fluidic channel according to one embodiment of the invention.
Figure 19:
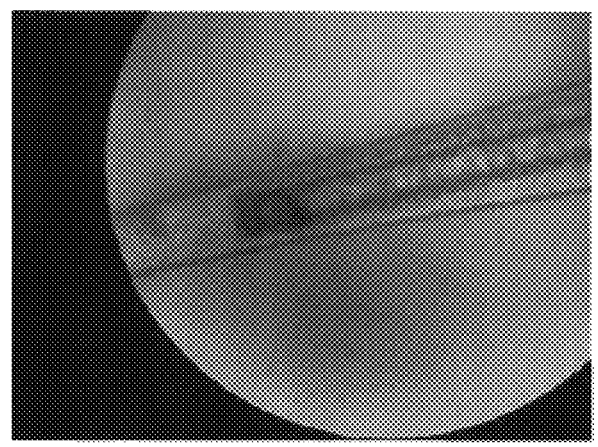
FIG. 19, in accordance with an embodiment herein, shows sample cross section image of the outlet to the fluidic channel of a fabricated silicon electrode with SU-8 fluidic channel according to one embodiment of the invention.
Figure 20:
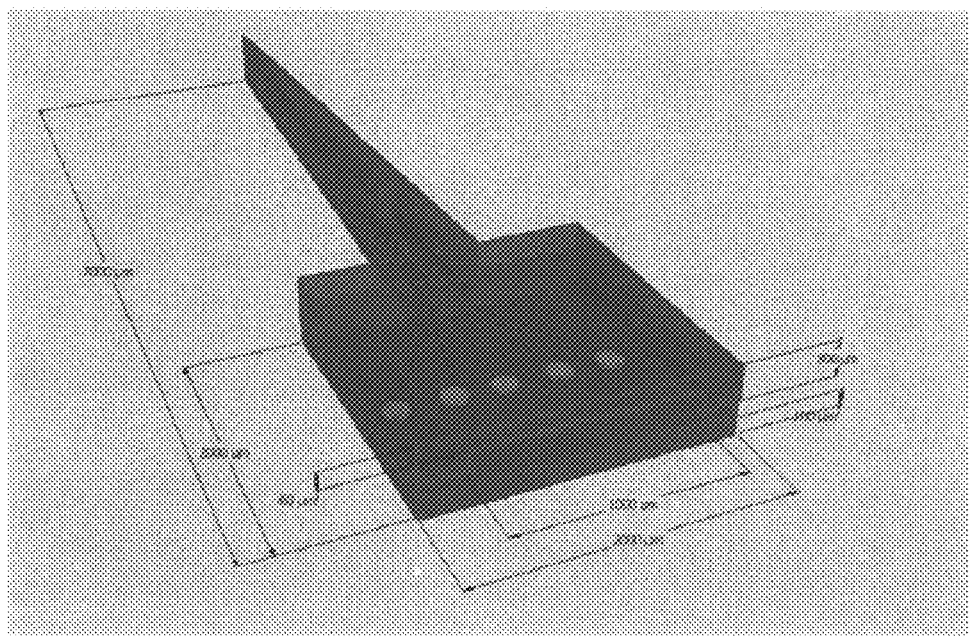
FIG. 20, in accordance with an embodiment herein, shows three dimensional view of the SU-8 microelectrode in accordance with one embodiment of the invention.

There is an established phenomenon known as—T-topping∥ that occurs with SU-8, where the top corners overhang. T-topping occurs due to low optical transmittance of SU-8 for wavelengths below 350 nm as wavelength below 350 nm penetrate only the surface of SU-8. This phenomenon is documented that Microchem Inc., who manufactures SU-8, suggests using a filter to eliminate wavelengths below 350 nm to obtain vertical sidewall profiles. However instead of eliminating, the lower wavelength light that is only able to penetrate the surface, it could be used to our advantage in sealing microchannels. The inventors used and developed this approach to fabricate fluidic channels in microelectrodes. FIG. 16 shows an example how using two wavelengths of UV can be used to fabricate the channel sidewalls and roof. The Higher wavelength (>350 nm) penetrates all the way through the SU-8 to define the probe shape and channel walls, while the lower wavelength (<320 nm) is used to partially crosslink upper portion of SU-8. FIG. 15 demonstrates the depth of penetration vs UV intensity while using a 312 nm band pass filter.

SU-8 Only Probe, Fabrication Method

Figure 23:
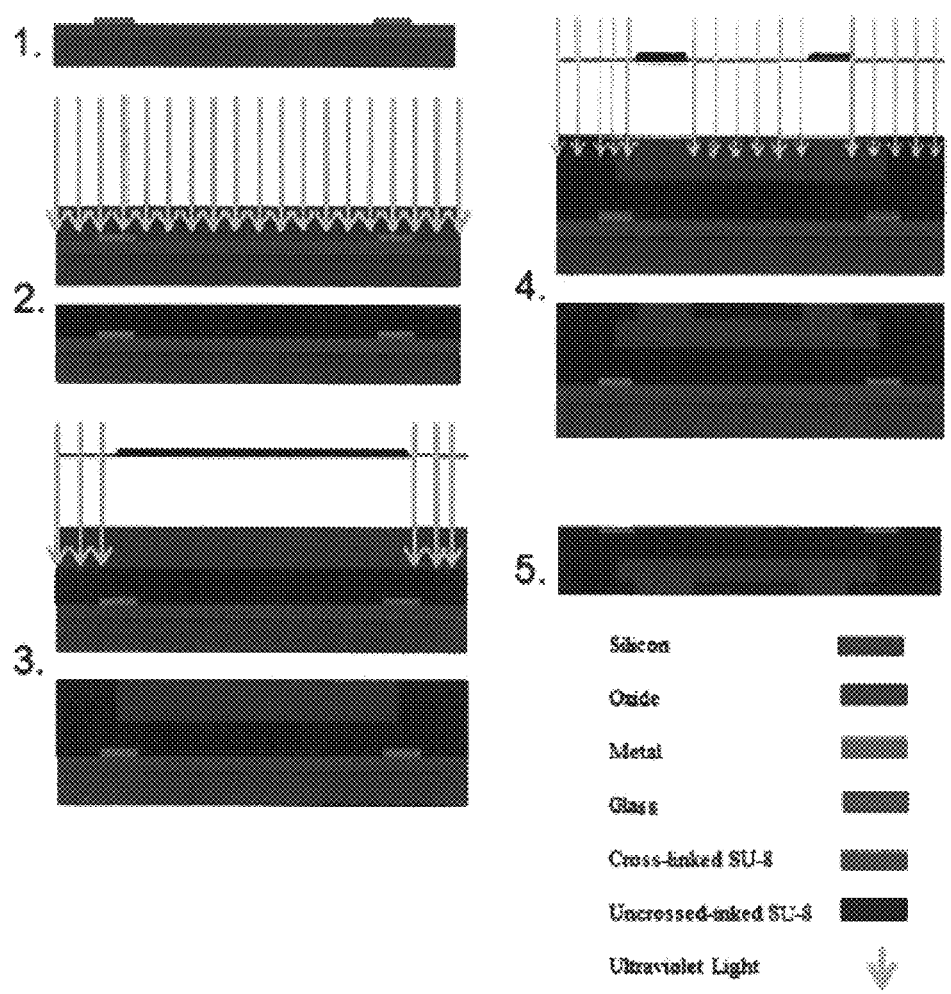
FIG. 23, in accordance with an embodiment herein, is cross-sectional views manufacturing process of SU-8 electrodes.
Figure 24:
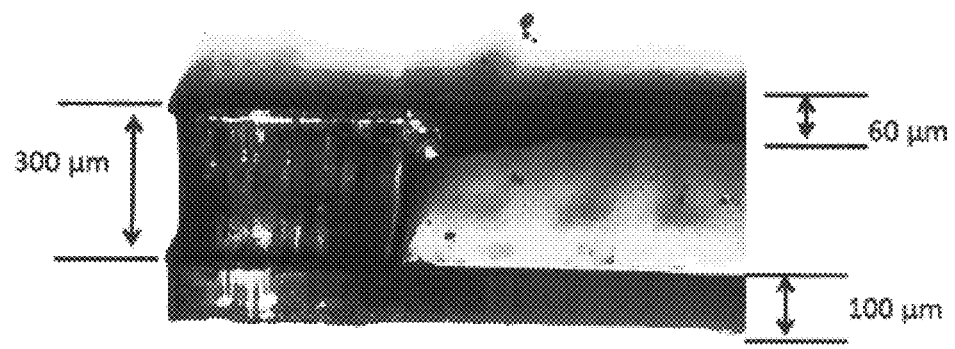
FIG. 24, in accordance with an embodiment herein, shows sample cross section image of the inlet to the fluidic channel of a fabricated SU-8 microelectrode in accordance to one embodiment of the invention.
Figure 25:
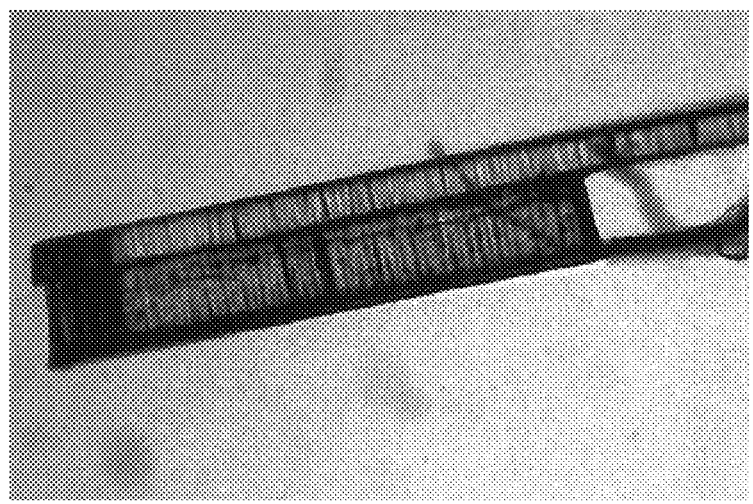
FIG. 25, in accordance with an embodiment herein, shows sample cross section image of the inlet to the fluidic channel of a fabricated SU-8 microelectrode in accordance to one embodiment of the invention.
Figure 26:
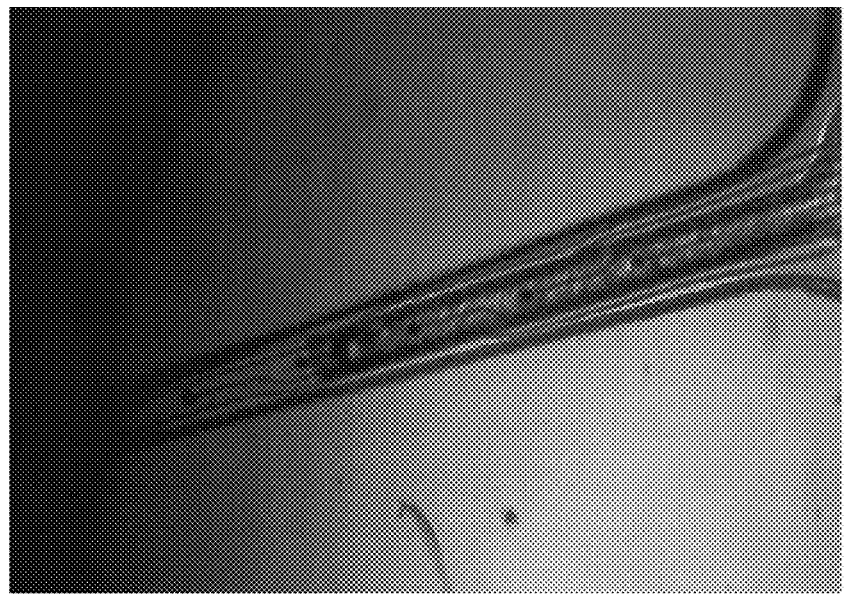
FIG. 26, in accordance with an embodiment herein, shows sample top view image of the outlet to the fluidic channel of a fabricated SU-8 microelectrode in accordance to one embodiment of the invention.

The main difference between the first two embodiments and the third is that the third is constructed completely out of SU-8, while the first two contain silicon. In one embodiment, a SU-8 fluidic channel is constructed on top of silicon, in another embodiment a SU-8 channel is constructed on SU-8. FIG. 23 displays the fabrication process of the SU-8 microchannel. The first step is to deposit a sacrificial layer, in our case we grew 2 μm of oxide. The next step was to pattern metal on oxide the inventors patterned 200 nm chrome but many other materials could be used including iridium oxide, gold, platinum, etc. The inventors did not deposit a thin passivation layer between the oxide and metal, but stoichiometric silicon nitride (SiCl2H2) could be deposited by low pressure chemical vapor deposition as it is not etched by BOE. If another sacrificial layer such as Aluminum is used then the passivation layer can be adjusted accordingly by reference of etch rates of materials. The next step was pattern the bottom of the channel and probe shape, by spinning 100 μm of SU-8 2050 and exposing it to 300 mJ/cm2 of 365 nm through a mask (FIG. 21 Top). The SU-8 was not developed at this time, to keep the surface planer, next a 300 μm layer of SU-8 2100 was spun and exposed to 500 mJ/cm2 of 365 nm light to define channel walls and probe shape (FIG. 21 Middle). To define the roof, the same layer was exposed to 720 mJ/cm2 of 365 nm light that was filtered through a band passed 312 nm filter (FIG. 21 Bottom). Finally, the probes were released soaking in buffered oxide etch. The sacrificial materials, metal layers, and dimensions can easily be changed with anyone skilled in the art. In addition, a SU-8 microelectrode without a fluidic channel could be easily constructed by using various methods described above, but only using one mask and exposure.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art.

Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein.

Accordingly, embodiments of the present invention are not limited to that precisely as shown and described.

The invention claimed is:

1. A flexible microelectrode, comprising:
   i. a bottom layer that forms a floor for an embedded fluidic channel;
   ii. a middle layer comprising:
      a front surface comprising one or more electrodes;
      a back surface comprising the embedded fluidic channel;
      wherein the fluidic channel comprises an inlet and an outlet; and
      wherein fluid can be injected from the inlet to the outlet for applications comprising electrophysiological experiments, drug delivery, and/or chemical release to prevent reactive cellular response; and
   iii. a top layer that forms the roof of the embedded fluidic channel, inlet, and outlet, wherein the inlet and outlet extend through the top layer;
   and wherein the bottom layer, middle layer and top layer of the microelectrode are constructed out of SU-8.

2. The microelectrode of claim 1, wherein the embedded fluidic channel is photolithographically fabricated.

3. A device, comprising:
   an implantable flexible microelectrode including a fluidic channel, wherein the microelectrode comprises:
   i. a bottom layer that forms a floor for the embedded fluidic channel;
   ii. a middle layer comprising:
      a front surface comprising one or more electrodes;
      a back surface comprising the fluidic channel;
      wherein the fluidic channel comprises an inlet and an outlet; and
      wherein fluid can be injected from the inlet to the outlet for applications comprising electrophysiological experiments, drug delivery, and/or chemical release to prevent reactive cellular response; and iii. a top layer that forms the roof of the embedded fluidic channel, inlet, and outlet, wherein the inlet and outlet extend through the top layer;

and wherein the bottom layer, middle layer and top layer of the microelectrode are constructed out of SU-8.

4. The device of claim 3, wherein the microelectrode is a neural implant.

5. The device of claim 3, wherein the fluidic channel is photolithographically fabricated in the microelectrode.

6. The device of claim 3, wherein the device is adapted to be implantable in an individual to deliver one or more factors that has the capability to mitigate immune response, tissue encapsulation, and/or enhance neural growth or peripheral nerves.

7. A method of implanting a neural device in an individual, comprising:

providing a neural device comprising an implantable flexible microelectrode including a fluidic channel; and implanting the neural device in the individual, wherein the neural device comprises:

i. a bottom layer that forms a floor for the fluidic channel;
ii. a middle layer comprising:
   a front surface comprising one or more electrodes;
   a back surface comprising the fluidic channel;
   wherein the fluidic channel comprises an inlet and an outlet; and
   wherein fluid can be injected from the inlet to the outlet for applications comprising electrophysiological experiments, drug delivery, and/or chemical release to prevent reactive cellular response; and
iii. a top layer that forms the roof of the fluidic channel, inlet, and outlet, wherein the inlet and outlet extend through the top layer;

and wherein the bottom layer, middle layer and top layer of the microelectrode are constructed out of SU-8.

8. The method of claim 7, wherein the neural device is implanted in conjunction with an overall treatment regimen for a neurological and/or nervous system disease or condition.

* * * * *